United States Patent
Gruter et al.

(10) Patent No.: US 9,145,526 B2
(45) Date of Patent: Sep. 29, 2015

(54) PROCESS FOR PREPARING FUEL COMPOSITIONS

(71) Applicant: Furanix Technologies B.V., Amsterdam (NL)

(72) Inventors: Gerardus Johannes Maria Gruter, Heemstede (NL); Edserd de Jong, Wageningen (NL)

(73) Assignee: FURANIX TECHNOLOGIES B.V., Amsterdam (NL)

( * ) Notice: Subject to any disclaimer, the term of this patent is extended or adjusted under 35 U.S.C. 154(b) by 0 days.

(21) Appl. No.: 13/874,776

(22) Filed: May 1, 2013

(65) Prior Publication Data

US 2013/0303792 A1    Nov. 14, 2013

Related U.S. Application Data

(62) Division of application No. 12/993,197, filed as application No. PCT/EP2009/003691 on May 19, 2009, now Pat. No. 8,435,313.

(30) Foreign Application Priority Data

May 19, 2008    (EP) .................................... 08075505

(51) Int. Cl.
*C07D 307/12*    (2006.01)
*C10L 1/02*    (2006.01)
*C10L 1/185*    (2006.01)
*C10L 10/12*    (2006.01)

(52) U.S. Cl.
CPC .................. *C10L 1/02* (2013.01); *C07D 307/12* (2013.01); *C10L 1/1855* (2013.01); *C10L 10/12* (2013.01); *Y02T 50/678* (2013.01)

(58) Field of Classification Search
CPC ...... C07D 307/12; C10L 10/12; C10L 1/1855
See application file for complete search history.

(56) References Cited

U.S. PATENT DOCUMENTS

| | | | |
|---|---|---|---|
| 2,153,135 A * | 4/1939 | Dickey et al. ................ | 428/393 |
| 2,196,747 A | 4/1940 | Dickey et al. | |
| 2,229,215 A | 1/1941 | Magruder et al. | |
| 2,321,311 A | 6/1943 | Mottlau et al. | |
| 2,599,338 A | 6/1952 | Lifson et al. | |
| 2,838,523 A | 6/1958 | Dunlop et al. | |
| 2,874,535 A | 2/1959 | Ayers et al. | |
| 2,993,334 A | 7/1961 | Burton | |
| 2,994,191 A | 8/1961 | Hamilton | |
| 3,021,204 A | 2/1962 | Arkell | |
| 3,342,838 A | 9/1967 | Noyori et al. | |
| 3,359,087 A | 12/1967 | Estes et al. | |
| 3,652,458 A | 3/1972 | Gobron et al. | |
| 4,153,578 A | 5/1979 | De Thomas et al. | |
| 4,316,359 A | 2/1982 | Sayles | |
| 4,522,630 A | 6/1985 | Seemuth | |
| 5,697,987 A | 12/1997 | Paul | |
| 5,925,152 A | 7/1999 | Barratt et al. | |
| 7,064,222 B2 | 6/2006 | Ahmed | |
| 2002/0053161 A1 | 5/2002 | Lacome et al. | |
| 2003/0069457 A1 | 4/2003 | Chen | |
| 2003/0110684 A1 | 6/2003 | Henly | |
| 2003/0154649 A1 | 8/2003 | Hull et al. | |
| 2006/0128844 A1 | 6/2006 | Sanborn et al. | |
| 2006/0180786 A1 | 8/2006 | Sapienza et al. | |
| 2007/0287845 A1 | 12/2007 | Lilga et al. | |

FOREIGN PATENT DOCUMENTS

| | | |
|---|---|---|
| EP | 0353777 A2 | 2/1990 |
| EP | 1321504 A2 | 6/2003 |
| GB | 1539287 | 1/1979 |
| WO | 2005087901 A2 | 9/2005 |
| WO | WO 2006122772 A1 * | 11/2006 |
| WO | 2007104514 A2 | 9/2007 |
| WO | 2008013922 A1 | 1/2008 |

OTHER PUBLICATIONS

Newth, F.H., et al. "The Conversion of Sucrose into Furan Compounds. Part IV. Some Aminotetrahydrofuran Derivatives." Journal of the Chemical Society. (1948), pp. 155-158.*

(Continued)

*Primary Examiner* — Andrew D Kosar
*Assistant Examiner* — John S Kenyon
(74) *Attorney, Agent, or Firm* — Hoffman & Baron, LLP

(57) ABSTRACT

A process for the preparation of a ring-hydrogenated alkyl furfuryl ether of the general formula (I) or a mixture of such ethers: (I) R"-TF—CH2-O—R where TF represents a 2,5-disubstituted tetrahydrofuran ring, where each R independently represents a hydrocarbyl group having from 1 to 20 carbon atoms and where each R" independently represents a methyl group, a hydroxymethyl group, the product of an aldol condensation reaction or an alkoxymethyl group of the general formula (II): (II) —CH2-O—R' where each R' independently represents a hydrocarbyl group having from 1 to 20 carbon atoms, the process including the step of reacting a 5-(alkoxymethyl)furfural of the general formula (III) or a 2,5-bis(dialkoxymethyl)furan of the general formula (IV) under hydrogenation conditions: (III) R'—O—CH2-F—CH=O (IV) R'—O—CH2-F—CH2-O—R" to form said ring-hydrogenated alkyl furfuryl ether of the general formula (I) or a mixture of said ethers wherein F represents a 2,5-disubstituted furan ring, and R', and R" have the definitions as described above.

5 Claims, 1 Drawing Sheet

(56) References Cited

OTHER PUBLICATIONS

Grogan, G., et al. "Diastereoselective hydroxylation and reduction of derivatised tetrahydrofurans by Beauveria bassiana." Biotechnology Letters. (2001), vol. 23, pp. 119-124.*
"Alkane." © Feb. 2007. Available from: < http://web.archive.org/web/20070214134032/http://en.wikipedia.org/wiki/Alkane >.*
Cope, A.C., et al. "Aminoalcohols Containing the 8-Oxa-3-azabicyclo[3.2.1]octane Ring System and Their Benzoates." Journal of the American Chemical Society (1955), vol. 77, pp. 393-396, IDS of May 1, 2013.*
Schiavo, V., et al. "Hydrogenation catalytique du 5-hydroxymethylfurfural en milieu aqueux." Bull. De La Societe Chimique de France. (1991), pp. 704-711, IDS of May 1, 2013.*
Roman-Leshkov, Y., et al. "Production of Dimethylfuran for Liquid Fuels From Biomass-Derived Carbohydrates." Nature. (2007), vol. 447, pp. 982-986.*
"Carbohydrates." © Dec. 2006. Available from: <http://web.archive.org/web/20061230203523/http://users.rcn.com/jkimball.ma.ultranet/BiologyPages/C/Carbohydrates.html >.*
W.R. Kirner: "Alpha-Tetrahydrofurfuryl Chloride and Alpha-tetrahydrofurfuryl Ethers" Journal of the American Chemical Society, vol. 52, Dec. 5, 1930, pp. 3251-3256, XP002498013.
Database Crossfire Beilstein, Beilstein Institute for Organic Chemistry, Frankfurt-Main, DE; 1950, XP002498014, Database accession No. BRN: 106201.
Database Beilstein, Beilstein Institute for Organic Chemistry, Frankfurt-Main, DE; 1950, XP002498015, Database accession No. BRN: 105046.
Cope et al: "Aminoalcohols Containing the 8-Oxa-3-azabicyclo [3.2.1.]octane Ring System and Their Benzoates", Journal of the American Chemical Society, American Chemical Society, Washington, DC.; US, US, vol. 77, Jan. 1, 1955, pp. 393-396, XP002378659, ISSN: 002-7863.
Schiavo V. et al: "Catalytic Hydrogenation of 5-(hydroxymethyl)furfural in aqueous medium" Bulletin De La Societe Chimique De France, Societe Francaise De Chimie, Paris, Jan. 1, 1991, pp. 704-711, XP008085941 ISSN: 0037-8968.
E. Taskinen: "Relative Thermodynamic Stabilities of 2-(Methoxymethylene)tetrahydrofuran and 5-Methoxymethy-2,3-Dihydrofuran" Journal of Physical Organic Chemistry, vol. 8, 1995, pp. 1-4, XP002517340.
Tyrlik S S K et al: "Selective dehydration of glucose to hydroxymethylfurfural and a one-pot synthesis of a 4-acetylbutyrolactone from glucose and trioxane in solutions of aluminium salts", Carbohydrate Research, Elsevier Scientific Publishing Company, Amsterdam, NL, vol. 315, No. 3-4, Feb. 28, 1999, pp. 268-272, XP004174265, ISSN: 0008-6215, p. 270, right-hand column.
Roman-Leshkov Y. et al.: "Production of Dimethylfuran for Liquid Fuels from Biomass-Derived carbohydrates" Nature, Nature Publishing Group, London, UK, vol. 447, Jun. 21, 2007, pp. 982-986, XP002469198, ISSN: 0028-0836, figures 1, 2.
Freudenrich, Craig PhD: "How Oil Refining Works", http://www.howstuffworks.com, © 1998-2007 HowStuffWorks, Inc. (4 pages).
PCT Notification of Transmittal of the International Preliminary Report on Patentability mailed Oct. 8, 2010.
PCT Written Opinion of the International Searching Authority, corresponding to PCT/EP2009/003691.
European Search Report for EP 08 07 5505 dated Mar. 2, 2009.
Communication from a foreign patent office for a counterpart foreign application, EP 09749656, dated Jun. 12, 2015.

* cited by examiner

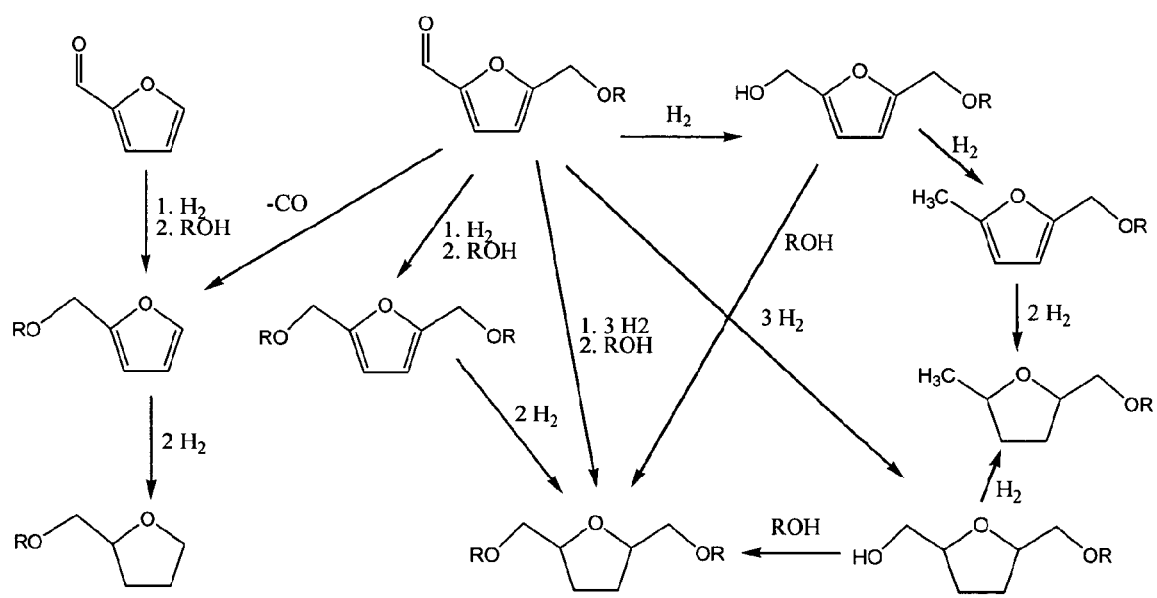

PROCESS FOR PREPARING FUEL COMPOSITIONS

CROSS-REFERENCE TO RELATED APPLICATIONS

This application is a divisional application of U.S. application Ser. No. 12/933,197, filed Nov. 17, 2010, which is the National Stage of International Application No. PCT/EP2009/003691, filed May 19, 2009, which claims the benefit of European Application No. EP 08075505.1, filed May 19, 2008, the contents of all of which are incorporated by reference herein.

TECHNICAL FIELD

This invention concerns a fuel composition and a component, which may be used as such or in a blend of fuels (e.g., in an amount from 1 to 100 vol %). The expression "fuel component" as used hereinafter includes both the use as fuel or as component in a blend of fuels. In particular it concerns an aviation fuel component. Also disclosed are processes for preparing these fuel components. More in particular, this invention concerns biobased fuel components.

BACKGROUND ART

Gasoline, diesel and kerosene are the most commonly used liquid transportation fuels. It is known that aviation fuel is a specialized type of petroleum-based fuel used to power aircraft. It is generally of a higher quality than fuels used in less critical applications such as heating or road transport, and often contains additives to reduce the risk of icing or explosion due to high temperatures, amongst other properties. Most aviation fuels available for aircraft are kinds of petroleum spirit used in engines with spark plugs i.e. piston engines and Wankel rotaries or fuel for jet turbine engines which is also used in diesel aircraft engines.

Aviation fuels consist of blends of over a thousand chemicals, primarily hydrocarbons (paraffins, olefins, naphthenes, and aromatics) as well as additives such as antioxidants and metal deactivators, and impurities. Principal components include n-octane and isooctane. Like other fuels, blends of Aviation fuel used in piston engined aircraft are often described by their octane rating. The net energy content for present day aviation fuels depends on their composition. Some typical values are: Avgas, 43.7 MJ/kg or 31.0 MJ/L; Wide-cut jet fuel, 43.5 MJ/kg or 33.2 MJ/L, and Kerosene type jet fuel, 43.8 MJ/kg or 35.1 MJ/L.

Outside former communist areas, there are currently two main grades of turbine fuel in use in civil commercial aviation: Jet A-1 and Jet A, both are kerosene type fuels. There is another grade of jet fuel, Jet B which is a wide cut kerosene (a blend of gasoline and kerosene) but it is rarely used except in very cold climates. Jet A-1 is a kerosene grade of fuel suitable for most turbine engined aircraft. It is produced to a stringent internationally agreed standard, has a flash point above 38° C. (100° F.) and a freeze point maximum of −47° C. Jet A is a similar kerosene type of fuel as Jet A-1 but with a higher freeze point maximum (−40° C.). Jet B is a distillate covering the naphtha and kerosene fractions. It can be used as an alternative to Jet A-1 where its better cold weather performance is important.

JP-4 is the military equivalent of Jet B with the addition of corrosion inhibitor and anti-icing additives. JP-5 is a high flash point kerosene. Finally, JP-8 is the military equivalent of Jet A-1 with the addition of corrosion inhibitor and anti-icing additives.

As mentioned, aviation fuel typically contains additives added to the fuel in very small quantities, usually measurable only in parts per million, to provide special or improved qualities. The quantity to be added and approval for its use in various grades of fuel is strictly controlled by the appropriate specifications. A few additives in common use are as follows:

1. Anti-knock additives reduce the tendency of gasoline to detonate. Tetra-ethyl lead (TEL) is the only approved anti-knock additive for aviation use and has been used in motor and aviation gasolines since the early 1930s.
2. Anti-oxidants prevent the formation of gum deposits on fuel system components caused by oxidation of the fuel in storage and also inhibit the formation of peroxide compounds in certain jet fuels.
3. Static dissipater additives reduce the hazardous effects of static electricity generated by movement of fuel through modern high flow-rate fuel transfer systems. Static dissipater additives do not reduce the need for 'bonding' to ensure electrical continuity between metal components (e.g. aircraft and fuelling equipment) nor do they influence hazards from lightning strikes.
4. Corrosion inhibitors protect ferrous metals in fuel handling systems, such as pipelines and fuel storage tanks, from corrosion. Some corrosion inhibitors also improve the lubricating properties (lubricity) of certain jet fuels.
5. Fuel System Icing Inhibitors (Anti-icing additives) reduce the freezing point of water precipitated from jet fuels due to cooling at high altitudes and prevent the formation of ice crystals which restrict the flow of fuel to the engine. This type of additive does not affect the freezing point of the fuel itself. Anti-icing additives can also provide some protection against microbiological growth in jet fuel.
6. Metal de-activators suppress the catalytic effect which some metals, particularly copper, have on fuel oxidation.
7. Biocide additives are sometimes used to combat microbiological growths in jet fuel, often by direct addition to aircraft tanks; as indicated above some anti-icing additives appear to possess biocidal properties.
8. Thermal Stability Improver additives are sometimes used in military JP-8 fuel, to produce a grade referred to as JP-8+100, to inhibit deposit formation in the high temperature areas of the aircraft fuel system.

As mentioned above, alcohol, alcohol mixtures and other alternative fuels may be used experimentally but are not generally available.

Although alternative aviation fuels are not general available, there are nonetheless many patents and scientific articles on (aviation) fuels containing for instance furan derivatives such as furfural, furfuryl alcohol, methylfuran, and dimethylfuran. The most important examples are summarized below.

Already in U.S. Pat. No. 2,599,338, fuel compositions are described containing tetrahydro furfuryl alcohol. The presence of this component reduced the loss in speed due to icing both in motor fuel and in an aviation fuel.

Recently, in WO2008013922, fully renewable engine fuels were described that are said to be derived completely from biomass sources. The fully renewable engine fuel is comprised of one or more low carbon number esters derived from ethanol, one or more pentosan-derivable furans, one or more aromatic hydrocarbons, one or more C4-C10 straight chain alkanes derivable from polysaccharides, and one or more bio-oils. In addition, the fuel may contain triethanolamine. Such a lower octane renewable fuel may be utilized, for example, in automobile fuel, 100 LL aviation fuel applications, and turbine engine applications. These ethanol-based, fully renewable fuels may be formulated to have a wide range of octane values and energy, and may effectively be used to replace 100LL aviation fuel (known as "aviation gasoline" or "AvGas"), as well as high octane, rocket, diesel, and turbine engine fuels.

As discussed in this reference, the inherent energy contained within gasoline is directly related to mileage, not to octane number. Automobile gasoline has no energy specification, hence no mileage specification. In contrast, aviation fuels, a common example being 100 LL (100 octane low lead), do have an energy content specification. This translates to aircraft range and to specific fuel consumption. Aircraft cannot compromise range. For this reason, energy content is equally important as MON values. It should be realized, however, that the aforementioned ethanol-based fuels are produced through fermentation of food crops and such and therefore compete with the production of food products. The generation of biofuel from food crops is widely discussed, given the pressure it will put on land, prices of food and the hunger problem.

Furan derivatives have indeed been used for various purposes in fuel compositions. In e.g., US20060180786A tetrahydrofurfuryl acetate and other derivatives have been described as pour point depressant for jet fuel/diesel fuel compositions. More specifically, this reference provides a method for lowering the pour point of biodiesel, said method comprising preventing or reducing crystallization of fatty acids, esters or alkaline salts of fatty acids in the biodiesel product by adding to said biodiesel an effective crystallization reducing or preventing amount of a composition, said composition comprising a.o. tetrahydrofurfuryl acetate and tetrahydrofurfuryl tetrahydrofuroate. Indeed, as antifreeze component, furfuryl alcohol has already been described in U.S. Pat. No. 2,229,215.

Furan derivatives have been suggested also for use in hypergolic propellants. A hypergolic propellant is either of the two rocket propellants used in a hypergolic rocket engine, which spontaneously ignite when they come into contact. The two propellants are usually termed the "fuel" and the "oxidizer". Although hypergolic propellants tend to be difficult to handle, a hypergolic engine is easy to control and very reliable. In common usage, the terms "hypergol" or "hypergolic propellant" are often used to mean the most common such propellant combination, hydrazine plus nitrogen tetroxide, or their relatives. Examples of furan derivatives in hypergolic propellants may be found in U.S. Pat. No. 4,316,359, U.S. Pat. No. 2,994,191, U.S. Pat. No. 2,993,334, and U.S. Pat. No. 2,874,535.

U.S. Pat. No. 4,339,245 describes a gasoline composition containing at least one antiknock compound selected from the group consisting of furfuryl acetate, ethyl furfurylacrylate, methyl furoate, and ethyl furoate. This case is not specific to aviation fuels. Similar cases on antiknock components, cetane improvers, or component to improve the octane rating may be found in U.S. Pat. No. 3,359,087, U.S. Pat. No. 3,021,204, EP1321504, WO2005087901, U.S. Pat. No. 5,925,152, U.S. Pat. No. 5,697,987 (which describes 2-methyltetrahydrofuran as an anti-knock component for spark ignition motor fuel composition at levels between 15-55%), U.S. Pat. No. 4,522,630, U.S. Pat. No. 2,321,311 (which discloses a motor fuel composition comprising a mixture of gasoline hydrocarbons adapted as a base fuel for spark-ignition engines improved in antiknock value by an addition of a substantial amount at least 1% by volume of a heterocyclic compound containing a furane nucleus and selected from the group consisting of furane, alkyl furanes, furfuryl alcohols, furfuryl amines, and the saturated derivatives thereof, said heterocyclic compound boiling in the range of said base fuel), US2003110684 and many other references.

From US2003154649 a method is known for reducing the vapor pressure of a C3 to C12 hydrocarbon-based motor fuel composition for a conventional spark ignition internal combustion engine comprising combining: (a) a hydrocarbon component comprising C3 to C12 hydrocarbon fractions; (b) an ethanol component comprising fuel grade ethanol, said ethanol component comprising 0.1% to 20% of the composition by volume; (c) an oxygen-containing heterocyclic compound having 5 to 8 carbon atoms selected from the group consisting of tetrahydrofurfuryl alcohol, tetrahydrofurfuryl acetate, dimethyltetrahydrofuran, tetramethyltetrahydrofuran.

US2002053161 discloses the use of oxygenated compounds derived from tetrahydrofurfuryl as additives or for-mulation bases of gas-oils and leading to a significant lowering of particle emissions. The oxygenated compound has the formula THF—C—X—R in which —X— is chosen from —O— and —O—(CH2-O)n (n=1-20) and R is chosen from alkyl groups containing from 1 to 30 carbon atoms; and groups containing a tetrahydrofurfuryl unit (isopropyl, isobutyl, tertbutyl and tertamyl groups).

Unfortunately, such furane derivatives are relatively expensive to make, they are relative unstable and/or their physical/chemical properties (energy density, melting point, boiling points flash points viscosity) are suboptimal.

The prior art comprises additional references on the use of certain furfuryl derivatives as yarn conditioners (U.S. Pat. No. 2,196,747 and U.S. Pat. No. 2,153,135), as component of a heat pump (GB1539287) and as topic for study in various reactions (W. R. Kirner: "Alpha-Tetrahydrofurfuryl Chloride and Alpha-Tetrahydrofurfuryl Ethers", JACS, vol. 52, 1930, pages 3251-3256; Cope et al: "Aminoalcohols Containing the 8-Oxa-3-azabicyclo[3.2.1.]octane Ring System and Their Benzoates" JACS, vol. 77, 1955, pages 393-396; E. Taskinen: "Relative Thermodynamic Stabilities of 2-(Methoxymethylene)tetrahydrofuran and 5-Methoxymethyl-2,3-Dihydrofuran" J. of Physical Organic Chemistry, vol. 8, 1995, pages 1-4; Schiavo et al: "Catalytic hydrogenation of 5-(hydroxymethyl)furfural in aqueous medium", Bulletin de la Soc. Chimique de France, 1991, pages 704-711). As of the use of these furfuryl derivatives as components in fuels and particular in aviation fuels nothing is mentioned in this art.

Likewise, the substances 2,5-bis-methoxymethyltetrahydrofuran (Beilstein registry number 106201) and 2-hydroxymethyl-5-methoxymethyl-tetrahydrofuran (Beilstein registry number 105046) are known, but made by complicated processes without disclosing their use as fuel or fuel component (cf. XP002498014 and XP002498015).

Strongly increasing fossil fuel prices, security of supply issues and growing concerns about greenhouse gas emissions have intensified the search for and use of Bioenergy applications (solar, wind, biomass, geothermal etc). An important area is the transportation sector but unfortunately on the short term only limited renewable energy solutions are available.

From an environmental perspective hydrogen would be a very attractive fuel. Unfortunately, hydrogen is a very inconvenient energy storage medium. Thus, the density of hydrogen at room temperature and pressure is 0.00009 kg/m3. The density at 700 bar amounts to 57.5 kg/m3, with an energy density of Qv=120 MJ/kg. The density of gasoline is 740 kg/m3, Qv=44 MJ/kg. Although per kg, hydrogen has a 120/44=2.7× higher energy density than gasoline, because of the low mass per volume, even at 700 bars hydrogen has only (2.7*(57.5/740)) 21% of the energy content of gasoline. In addition, compression to 700 bar requires 20% of fuel energy. Hydrogen can also be stored as a liquid in a cryogenic tank. However, when stored at −253° C. the density is still only 70 kg/m3. This liquefaction requires 40% of fuel energy. The required fuel tanks (for both pressurization and liquefaction) are heavy and expensive. A cryogenic tank to store 8 kg fuel weighs 120 kg—high pressure tanks are significantly heavier! A major disadvantage of liquefaction is that half the fuel boils off in 9 days!

A further solution has been to store hydrogen in mineral or organic materials. Metallocarboranes have been able to reversibly store 50 kg/m3 hydrogen (NREL annual hydrogen report 2007). These materials are however prohibitively expensive. So far the strategies for hydrogen storage via reaction or complexation with "host" materials required release of hydrogen upon use.

Another fuel considered attractive from an environmental perspective is biofuel (i.e., fuels of bioorganic origin as opposed to fuels of petroleum origin).

Biofuel can be broadly defined as solid, liquid, or gas fuel consisting of, or derived from recently dead biological material, most commonly plants. This distinguishes it from fossil fuel, which is derived from long dead biological material. Biofuels are used globally. The most common use for biofuels is automotive transport. The use of renewable biofuels in lieu of fossil fuels is said to reduce greenhouse gas emissions and increase energy security.

One of the greatest technical challenges is to develop ways to convert biomass energy specifically to liquid fuels for transportation. To achieve this, the two most common strategies are:
1. To grow sugar crops (sugar cane, and sugar beet), or starch (corn/maize), and then use yeast fermentation to produce ethanol (ethyl alcohol).
2. To grow plants that (naturally) produce oils, such as palm, rapeseed, soy, algae, or jatropha. When these oils are heated, their viscosity is reduced, and they can be burned directly in a diesel engine, or the oils can be chemically processed to produce fuels such as biodiesel.

Increased demand for biofuels, particularly in America and Europe has led to deforestation and food shortages. This is increasingly making biofuels into a political issue throughout the world. Recently, inventors of Furanix Technologies B.V. have developed an alternative route to biofuels, based on 5-alkoxymethyl furfural derivatives that are prepared by reacting a fructose and/or glucose-containing starting material with an alcohol in the presence of a catalytic or sub-stoichiometric amount of heterogeneous acid catalyst. See WO2007104514. The catalysts may be employed in a continuous flow fixed bed or catalytic distillation reactor. The ethers can be applied as a fuel or fuel additive.

As indicated in this prior patent application, the conversion of one glucose molecule by fermentation into two molecules of ethanol and two molecules of CO2 has drawbacks especially in view of atom economy, the low energy density of ethanol (7.7 kWh/kg or 6.1 kWh/L), its relative low flash point (13 degrees Celsius), hygroscopic nature and corrosiveness.

For fuel and aviation fuel in particular, products of increased energy density, flash point, and melting point are required. Ideally, these products should be based on biomass or biomass products. On the other hand, the preparation of these (aviation) biofuels should be economically feasible and energetically acceptable. The products should be at least as good as methylfuran and dimethylfuran, that have been proposed as aviation fuel in the past, but which production-routes were non-economic to date.

Interestingly, the current inventors have found a new class of compounds that may be used as fuel and/or as fuel additive. These compounds may be produced by proven technologies, using starting materials based on biomass or biomass products.

In fact the current inventors have realised that unlike the products resulting from mineral oil, biomass derived furans are very high in unsaturation. This enables the use of these compounds as a cheap hydrogen storage medium, without the challenging hydrogen release requirement! Both the hydrogen as well as the furan "storage host" can be used as an economic fuel. Moreover, it has now been realized to prepare biomass derived fuel components that meet the requirements concerning flash point and freeze point maximum whilst providing a high energy density. In other words, the new fuel components are uniquely suitable for use as aviation fuel.

SUMMARY OF THE INVENTION

Accordingly, the invention provides a fuel composition comprising a ring-hydrogenated alkyl furfuryl ether of the general formula (I):

$$R''\text{-TF---CH2-O---R} \quad (I)$$

wherein TF represents a 2,5-disubstituted tetrahydrofuran ring, wherein each R independently represents a hydrocarbyl group having from 1 to 20 carbon atoms and wherein each R" independently represents a methyl group, a hydroxymethyl group, the product of an aldol condensation reaction or an alkoxymethyl group of the general formula (II):

$$\text{---CH2-O---R'} \quad (II)$$

wherein each R' independently represents a hydrocarbyl group having from 1 to 20 carbon atoms, optionally in combination with other oxygenated compounds derived from furan and optionally in combination with diesel fuels of petroleum origin or diesel fuels of bioorganic origin. The invention also provides novel and useful ring-hydrogenated alkoxymethyltetrahydrofuran ethers. Moreover, these ring-hydrogenated alkoxymethyltetrahydrofuran ethers disclosed herein have never been used as fuel component, and therefore the use of these ethers has also been claimed as an invention. A further embodiment of the current invention is the process for preparing these components. Finally, the use of a 5-(alkoxymethyl)furfural, and/or a 2,5-bis(alkoxymethyl)furan as hydrogen storage molecules, in particular for fuel purposes is believed to be novel and inventive and is therefore claimed as a further embodiment of the current invention. In other words, also is claimed a method for energetically enriching fuel compositions comprising oxygenated compounds derived from furan, wherein the oxygenated compounds derived from furan is a 5-alkoxymethylfurfural of the general formula (III) or a 2,5-bis(dialkoxymethy)furan of the general formula (IV) and the fuel is enriched by storing additional hydrogen therein by hydrogenating said 5-alkoxymethylfurfural and/or 2,5-bis(dialkoxymethyl)furan.

BRIEF DESCRIPTION OF THE DRAWINGS

FIG. 1 depicts different routes to come to the three types of disubstituted R"-TF—CH2-O—R compounds.

DETAILED DESCRIPTION OF THE INVENTION

The synthesis of a 5-(alkoxymethyl)furfural is already described in the international application mentioned above, WO2007104514, included herein by reference. This application provides a very interesting route to such furfural derivatives by conversion of biomass. On the other hand, the melting point, the energy density and the blending properties of e.g. 5-(ethoxymethyl)furfural (EMF) leaves room for improvement. This is of particular importance in aviation fuels, which require amongst others a flash point above 38° C. and a freezing point maximum of −47° C. (Jet A-1 standards).

For the preparation of the fuel components of the current invention, any 5-(alkoxymethyl)furan may be used, including mixtures of different 5-(alkoxymethyl)furans as well as mixtures of a 5-(alkoxylmethyl)furan and other biomass derivatives. In FIG. 1 the different routes to come to the 3 types of disubstituted R"-TF—CH2-O—R are represented. Included on the left side is also the route to prepare a monosubstituted derivative, which may be present in the final fuel composition.

Thus, each carbyl group may have from 1 to 20 carbon atoms. It may be linear or branched. Preferably each carbyl group contains from 1 to 12 carbon atoms, more preferably from 1 to 6 carbon atoms, more preferably from 1 to 4 carbon atoms.

Thus, by converting a 5-(alkoxymethyl)furfural under ordinary ring-hydrogenation conditions, fuel components as defined in claim 1 are prepared. Alternatively, a symmetric or asymmetric 2,5-bis(alkoxymethyl)furan may be used, which can also be made from biomass. Such starting material can for instance be made using the technology of European Patent Application No. 07075777.8. That invention concerns a method for the manufacture of a 5-substituted 2-(alkoxymethyl)furan (or a mixture of such furans) by reacting a starting material comprising at least a 5-substituted furfural or a mixture thereof with hydrogen in the presence of an alcohol and a catalyst system.

Typical alcohols in respect of this embodiment include C1 to C20 alcohols that may be linear or branched, and/or pure or used as mixture. C1 to C4 alcohols are most preferred. As a result, fuel components based on 2-ethoxymethyl-5-methoxymethyltetrahydrofuran, bis-2,5-(ethoxymethyl)tetrahydrofuran and bis-2,5-(methoxymethyl)tetrahydrofuran are preferred.

In each of the aforementioned hydrogenation reactions, typically a mixture of products is obtained. For instance, the hydrogenation of 5-(ethoxymethyl)furfural (EMF) may result in the hydrogenation of the aldehyde group (into a hydroxymethyl group or methyl group or in the presence of an alcohol and an acid catalyst to an alkoxymethyl group) and/or in the hydrogenation of the furan ring (which proceeds through de formation of a dihydrofuran ring until a tetrahydrofuran ring is obtained). During the hydrogenation reaction, if an alcohol is present, also ether products may be formed. For (aviation) fuel each of these components, except the starting EMF and the hydroxymethyl alcohols, are useful.

The fully hydrogenated products are preferred, as their energy density is the highest. Also, they mix better with fossil fuels. In such a case a selective hydrogenation catalyst will not be necessary. Selective hydrogenation catalysts, however, may be used. For instance, the new products may actually come in the form of racemic mixtures or depending on the hydrogenation catalyst even in their R or S forms.

Once again, the current invention uniquely combines the principle of hydrogen storage and (biomass derived) fuel components to prepare new fuel components of even greater interest.

The catalytic hydrogenation of furan derivatives into their tetrahydrofuran analogs has been described in patents before. By way of example, some processes are listed hereafter.

Continuous vapor-phase processes have been disclosed in U.S. Pat. No. 7,064,222 using commercially-available catalysts, namely, a reduced copper-based catalyst consisting essentially of cupric oxide, chromium (III) oxide, manganese oxide and barium chromate and a reduced nickel-based catalyst consisting essentially of nickel, nickel (II) oxide, aluminum oxide and silica.

Hydrogenation of the furan ring of furfuryl alcohol has been described before using Ni or Cu catalysts on different kind of supports (U.S. Pat. No. 2,838,523, U.S. Pat. No. 3,652,458). In US2006128844 a method is described of preparing 2,5-bis(hydroxymethyl)tetrahydrofuran using a catalyst system comprising nickel and zirconium.

A catalytic process for the simultaneous synthesis of furfuryl alcohol and cyclohexanone by the hydrogenation of furfural and dehydrogenation of cyclohexanol respectively has been described in U.S. Pat. No. 7,015,359. The process comprising contacting a mixture of furfural and cyclohexanol with a Cu based catalyst of the formula xCu-yMgO-zCr2O3, wherein x, y and z are the amounts in terms of weight percent of Cu, MgO and Cr2O3 respectively.

From U.S. Pat. No. 4,459,419 a hydrogenation process is known, which comprising contacting 2,5-bis-(hydroxymethyl)furan with hydrogen in contact with a catalyst consisting essentially of zeolite support containing a catalytic amount of ruthenium in cationic form. Raney nickel and nickel have been claimed for the hydrogenation of furoic acid and HMF into tetrahydrofuroic acid and 2,5-bis-(hydroxymethyl)tetrahydrofuran (U.S. Pat. No. 3,342,838, U.S. Pat. No. 4,153,578)

In US2007287845 a method is provided of reducing hydroxymethylfurfural (HMF) with a catalyst containing at least one metal selected from Ni, Co, Cu, Pd, Pt, Ru, Ir, Re and Rh.

In US2003069457 a non-chrome, copper-containing catalyst, Cu—Al—O and method of preparing the same are provided. The Cu—Al—O catalyst can be employed in applications in place of Cu/Cr, or other copper based catalysts.

On the other hand, the hydrogenation of a (biomass-derived) 5-(alkoxymethyl)furfural or 2,5-bis(alkoxymethyl)furan has not been described before. The same is true for the reaction of furfural with hydrogen in the presence of an alcohol to form the corresponding alkoxymethyltetrahydrofuran. Put in different words, the current invention also provides the use of (biomass-derived) 5-(alkoxymethyl)furfural or 2,5-bis(alkoxymethyl)furan as hydrogen storage. In other words, the current invention also provides a method for energetically enriching fuel compositions, comprising oxygenated compounds derived from furan, wherein the oxygenated compounds derived from furan is a 5-alkoxymethylfurfural of the general formula (III) or a 2,5-bis(dialkoxymethyl)furan of the general formula (IV) and the fuel is enriched by storing additional hydrogen therein by hydrogenating said 5-alkoxymethylfurfural and/or 2,5-bis(dialkoxymethyl)furan.

Suitably, any of the known hydrogenation processes may be used. More preferably, the hydrogenation is carried out at elevated temperatures, in the presence of a suitable homogeneous or heterogeneous catalyst. Use of a heterogeneous (i.e., solid or supported) catalyst is particularly advantageous from a process perspective (e.g., in continuous processes) and a cost perspective (less loss of catalyst). The hydrogenation catalyst for use in the present invention may therefore be selected from heterogeneous catalysts containing base metals Ni, Cu, Co and Cr and/or precious metals Pt, Pd, Rh and Ru. Most preferably, the catalyst is a heterogeneous catalyst containing Ni, Pd or Rh supported on an inert and mechanically stable carrier, preferably alumina, titanium dioxide, silica, aluminium silicates, zeolites, magnesium silicate and active carbon, preferably silica or carbon.

The temperature at which the hydrogenation process is performed may vary, but in general it is preferred that the reaction is carried out at a temperature from 50 to 400 degrees Celsius, preferably from 100 to 250 degrees Centigrade, more preferably from 100 to 150 degrees Celsius. In general, temperatures higher than 300 degrees Centigrade are less preferred as the selectivity of the reaction deteriorates at high temperatures. Exceptions to this may be processes that are taking place at higher temperatures (such as 400 degrees C.) in the gas-phase. Performing the reaction below the lowest temperature is also less preferable because of the slow reaction speed.

The reaction is preferably carried out a hydrogen pressure of from 1 to 100 bar, or more preferably from 5 to 15 bar, where the molar ratio of hydrogen to furan derivative is not less than 5.

The catalyst can be added to the reaction mixture in an amount varying from 0.01 to 40 mole % drawn on the starting material preferably from 0.1 to 30 mole %, more preferably from 1 to 20 mole %.

A solvent may be present, e.g., if it has been used as reaction medium in the synthesis of the starting materials.

The hydrogenation process may be performed in a continuous flow process. In that case, homogenous catalysts may be used and the residence time of the reactants in the flow process is between 0.1 second and 10 hours, preferably from 1 second to 1 hours, more preferably from 10 seconds to 10 minutes.

Alternatively, and according to the preferred embodiment, the continuous flow process is a fixed bed continuous flow process or a reactive (catalytic) distillation process with preferably a heterogeneous hydrogenation catalyst. To initiate or regenerate the heterogeneous catalyst or to improve performance, fresh catalyst or catalyst regenerators may be added to the feed of the fixed bed or reactive distillation continuous flow process. In a fixed bed process, the liquid hourly space velocity (LHSV) can be from 1 to 1000, preferably from 5 to 500, more preferably from 10 to 250 and most preferably from 25 to 100. Alternatively, the reactions may also be carried out in batch, using a single reactor vessel. Indeed, various modifications of this process may be used without departing from the gist of this invention.

EXAMPLES

The following examples are intended to further illustrate, without limiting, the processes of the invention.

Example 1

Ring and Aldehyde Hydrogenation

A teflon lined, 10 mL stainless steel batch reactor containing 150 mg (1.0 mmol) of 5-(ethoxymethyl)furfural in 1 mL dioxane and 10.3 mg of a Ni on silica catalyst (KataLeuna; Supplier ID: KL6504N) is pressurized to 50 bar of hydrogen and subsequently heated, under stirring, to 120° C. for 3 hours. After the reaction, de reactor is cooled quickly in an ice bath and depressurized. A sample is diluted with methanol for analysis of the products with GC and GC-MS. The analysis shows a 2-(ethoxymethyl)furfural conversion of 100%, a selectivity to 2-(ethoxymethyl)-5-(hydroxymethyl)tetrahydrofuran of 92%.

Example 2

Ring Hydrogenation (1)

A teflon lined, 10 mL stainless steel batch reactor containing 370 mg (2.0 mmol) of bis-2,5-(ethoxymethyl)furan in 1 mL methanol and 9.8 mg of a Ni on silica catalyst (KataLeuna; Supplier ID: KL6504N) is pressurized to 12.5 bar of hydrogen and subsequently heated, under stifling, to 100° C. for 4 hours. After the reaction, de reactor is cooled quickly in an ice bath and depressurized. A sample is diluted with methanol for analysis of the products with GC and GC-MS. The analysis shows a bis-2,5-(ethoxymethyl)furan conversion of 39%, and a selectivity to bis-2,5-(ethoxymethyl)tetrahydrofuran of 87%.

Example 3

Ring Hydrogenation (2)

A teflon lined, 10 mL stainless steel batch reactor containing 370 mg (2.0 mmol) of bis-2,5-(ethoxymethyl)furan in 1 mL methanol and 49.9 mg of a Ni on silica catalyst (KataLeuna; Supplier ID: KL6504N) is pressurized to 12.5 bar of hydrogen and subsequently heated, under stifling, to 100° C. for 4 hours. After the reaction, de reactor is cooled quickly in an ice bath and depressurized. A sample is diluted with methanol for analysis of the products with GC and GC-MS. The analysis shows a bis-2,5-(ethoxymethyl)furan conversion of 69%, and a selectivity to bis-2,5-(ethoxymethyl)tetrahydrofuran of 85%.

Example 4

Physical Characteristics of the 2-(alkoxymethyl)tetrahydrofuran and bis-2,5-(alkoxymethyl)tetrahydrofuran Compared to Jet A-1 Aviation Fuel and Dimethylfuran (where alkoxymethyl=methoxymethyl, ethoxymethyl, n-propoxymethyl, i-propoxymethyl, n-butoxymethyl, i-butoxymethyl or t-butoxymethyl

|  | Jet A-1 | Dimethylfuran | new fuel components |
|---|---|---|---|
| Aromatics (%) | 25 | 100 ? | 0-100 |
| Flash point (° C.) | 38 | −1.7 | up to 60 |
| Melting point (° C.) | −47 | −62 | −120--30 |
| Boiling point (° C.) | range | 92-94 | 80->200 |
| Density (15° C., kg/m3) | 775-840 | 900 | 850-1100 |
| Net heat of combustion (MJ/L) | 33 | 33 | 28-34 |

Example 5

Fuel Applications

Fuel Solubility

Fuel solubility is a primary concern for gasoline and diesel fuel applications. Not all highly polar oxygenates have good solubility in the current commercial gasoline and diesel fuels. Experiments show that all the new fuel components according to the present invention can be blended with kerosene, gasoline and diesel in all ratios. In a comparative set of experiments it was shown that 5-(t-butoxymethyl)furfural can be blended with commercial diesel up to 45%. At higher blend concentration, phase separation was observed. 5-(ethoxymethyl)furfural (EMF) is miscible up to 5 vol % with commercial diesel.

Cetane Number

Oxygenated fuel additives may reduce the natural cetane number of the base diesel fuel. A 0.1 vol % blend of 5-(methoxymethyl)tetrahydrofuran, and similar blend with 5-(ethoxymethyl)tetrahydrofuran were prepared with an additive free diesel fuel at an outside laboratory for cetane determination according to an ASTM D 6890 certified method. While the reference additive-free diesel showed an average cetane number of 52.5, surprisingly, 0.1 vol % of the 5-(alkoxymethyl)tetrahydrofuran blends showed an increase with 0.5-1.0 to an average cetane number of 53.0-53.5.

Oxidation Stability

Likewise, oxygenated fuel additives often reduce the oxidation stability of the base diesel fuel. A 0.1 vol % blend of 5-(methoxymethyl)tetrahydrofuran, and a similar blend with 5-(ethoxymethyl)tetrahydrofuran were prepared with an additive free diesel fuel at an outside laboratory for oxidation stability determination according to NF en ISO 12205 certified methods. Surprisingly, both the reference additive-free diesel and the 0.1 vol % 5-(alkoxymethyl)tetrahydrofuran blends showed the same oxidation stability, indicating that the addition of new fuel components according the present invention to an additive free diesel base fuel does not decrease the oxidation stability of the blend relative to the pure base diesel.

Example 6

Diesel Engine Testing

In a D9B diesel engine of a Citroen Berlingo test car, comparative testing is performed with normal commercial diesel as a fuel and the same commercial diesel to which 25 vol. % and 40 vol-% 5-(ethoxymethyl)furan was added, respectively 5-(ethoxymethyl)furan is added as a liquid and does not yield any mixing or flocculation problems at any blend ratio. The engine is run stationary with regular diesel initially, after which the fuel supply is switched to the 25 vol % 5-(ethoxymethyl)furan/diesel blend for 1.5 hours. After this time, the fuel supply is switched to the 40 vol % 5-(ethoxymethyl)furan/diesel blend for 1.5 hours.

The invention claimed is:

1. A process for the preparation of a ring-hydrogenated alkyl furfuryl ether of the general formula (I):

  (I)

wherein TF represents a 2,5-disubstituted tetrahydrofuran ring, wherein R independently represents a hydrocarbyl group having from 1 to 20 carbon atoms and wherein R" independently represents a methyl group, a hydroxymethyl group or an alkoxymethyl group of the general formula (II):

  (II)

wherein R' independently represents a hydrocarbyl group having from 1 to 20 carbon atoms, said process comprising the step of reacting a 5-(alkoxymethyl)furfural of the general formula (III) or a 2,5-bis(dialkoxymethyl)furan of the general formula (IV) under hydrogenation conditions:

  (III)

  (IV)

to form said ring-hydrogenated alkyl furfuryl ether of the general formula (I) wherein F represents a 2,5-disubstituted furan ring, and R' and R have the definitions as defined herein.

2. The process as claimed in claim 1, wherein the reacting step under hydrogenation conditions further comprises the step of contacting the 5-(alkoxymethyl)furfural of the general formula (III) or the 2,5-bis(dialkoxymethyl)furan of the general formula (IV) with hydrogen in the presence of a hydrogenation catalyst.

3. The process as claimed in claim 2, further comprising:
providing a homogeneous or heterogeneous hydrogenation catalyst wherein the reaction is carried out in the presence of said homogeneous or heterogeneous hydrogenation catalyst.

4. The process as claimed in claim 3, wherein the catalyst is a supported metal heterogeneous hydrogenation catalyst containing base metals Ni, Cu, Co and Cr and/or precious metals Pt, Pd, Rh and Ru supported on alumina, titanium dioxide, silica, aluminum silicates, zeolites, magnesium silicate and active carbon or, the catalyst is a heterogeneous catalyst containing Ni, Pd or Rh supported on silica or carbon.

5. The process as claimed in claim 3, wherein the reaction is carried out at a temperature from 50 to 400 degrees Celsius at a hydrogen pressure of from 1 to 100 bar, where the molar ratio of hydrogen to furan derivative is not less than 5.

* * * * *